(12) United States Patent
Wu et al.

(10) Patent No.: US 12,239,530 B2
(45) Date of Patent: Mar. 4, 2025

(54) DELIVERY CATHETER AND DELIVERY DEVICE FOR ARTIFICIAL VALVE

(71) Applicant: SHANGHAI MICROPORT CARDIOFLOW MEDTECH CO., LTD., Shanghai (CN)

(72) Inventors: Xuwen Wu, Shanghai (CN); Jie Mei, Shanghai (CN); Baozhu Gui, Shanghai (CN); Guoming Chen, Shanghai (CN); Yu Li, Shanghai (CN)

(73) Assignee: SHANGHAI MICROPORT CARDIOFLOW MEDTECH CO., LTD., Shanghai (CN)

( * ) Notice: Subject to any disclaimer, the term of this patent is extended or adjusted under 35 U.S.C. 154(b) by 889 days.

(21) Appl. No.: 17/418,118

(22) PCT Filed: Dec. 20, 2019

(86) PCT No.: PCT/CN2019/127067
§ 371 (c)(1),
(2) Date: Jun. 24, 2021

(87) PCT Pub. No.: WO2020/135262
PCT Pub. Date: Jul. 2, 2020

(65) Prior Publication Data
US 2022/0054265 A1    Feb. 24, 2022

(30) Foreign Application Priority Data
Dec. 27, 2018   (CN) .......................... 201811612802.2

(51) Int. Cl.
A61F 2/24    (2006.01)

(52) U.S. Cl.
CPC .......... *A61F 2/2436* (2013.01); *A61F 2/2466* (2013.01)

(58) Field of Classification Search
CPC ...... A61F 2/2436; A61F 2/2466; A61F 2/962; A61F 2/966; A61F 2250/0008;
(Continued)

(56) References Cited

U.S. PATENT DOCUMENTS

| 10,076,410 B2* | 9/2018 | Quijano ............... H03K 5/1252 |
| 2007/0208407 A1* | 9/2007 | Gerdts ...................... A61F 2/95 |
| | | 623/1.11 |

(Continued)

FOREIGN PATENT DOCUMENTS

| CN | 1961983 A | 5/2007 |
| CN | 103561807 A | 2/2011 |

(Continued)

*Primary Examiner* — Suzette J Gherbi
(74) *Attorney, Agent, or Firm* — Muncy, Geissler, Olds & Lowe, P.C.

(57) ABSTRACT

A prosthetic valve delivery catheter and device. The delivery catheter includes an outer sheath assembly and an inner sheath assembly. The outer sheath assembly includes a capsule in which a prosthetic valve can be received and an outer sheath fixedly connected at one end to the capsule. The inner sheath assembly includes an inner sheath and an anchor fixedly connected to the inner sheath. The inner sheath assembly is arranged within a lumen of the outer sheath assembly, and the capsule and the anchor form a circumferentially indexed fit therebetween. With this design, the anchor and the capsule can be driven to rotate under the action of circumferential rotation of the inner sheath, thus the matching between the prosthetic valve and a native valve annulus can be adjusted. Moreover, the capsule can be driven to move axially under actuation of the outer sheath to allow release of the prosthetic valve.

12 Claims, 4 Drawing Sheets

(58) Field of Classification Search
CPC .... A61F 2002/30024; A61F 2250/0021; A61F 2250/0025
See application file for complete search history.

(56) References Cited

U.S. PATENT DOCUMENTS

| | | | |
|---|---|---|---|
| 2011/0251675 | A1 | 10/2011 | Dwork |
| 2013/0030351 | A1* | 1/2013 | Belhe ................... A61F 5/0076 604/9 |
| 2013/0231735 | A1 | 9/2013 | Deem et al. |
| 2015/0223955 | A1* | 8/2015 | Li ..................... A61M 25/0136 606/108 |
| 2018/0000584 | A1* | 1/2018 | Duffy ................... A61F 2/2439 |
| 2018/0098848 | A1* | 4/2018 | Tran ...................... A61F 2/2436 |
| 2018/0256327 | A1* | 9/2018 | Perszyk ................ A61F 2/2436 |

FOREIGN PATENT DOCUMENTS

| | | |
|---|---|---|
| CN | 103118630 A | 5/2013 |
| CN | 209405022 U | 9/2013 |
| JP | 2016506795 A | 3/2016 |
| JP | 2018171463 A | 11/2018 |
| WO | WO-2011156533 A2 | 12/2011 |

\* cited by examiner

DELIVERY CATHETER AND DELIVERY DEVICE FOR ARTIFICIAL VALVE

TECHNICAL FIELD

The present invention relates to the field of medical instruments and, in particular to, a prosthetic valve delivery catheter and device.

BACKGROUND

With the development of social economy and the aging of the population, the incidence of valvular heart disease has increased significantly. Studies show that the incidence of valvular heart disease in elderly over 75 years has reached up to 13.3%. At present, traditional surgical treatment remains the first choice for patients with severe valvular disease. However, this means a high surgical risk and a high mortality for patients with advanced age, multiple organ diseases, a history of thoracotomy and poor cardiac function, and is even unsuitable for some patients. Transcatheter heart valve replacement has gained wide attraction from experts and academic researchers due to a wide variety of advantages including no need for open heart surgery, less trauma and rapid patient recovery.

SUMMARY OF THE INVENTION

Technical Problem

Heart valve replacement requires precise release of a prosthetic valve. Due to the high complexity of patients' anatomies, such prostheses are often designed with various irregular shapes. For example, in order to enable anchoring of a prosthetic valve in a target anatomy by a snug fit, a stent in the prosthesis may be designed to have a D-like, polygonal or another shape. Precise release of such a cross-sectionally irregular prosthetic valve into the target anatomy requires a delivery device capable of angular adjustment of the prosthetic valve. However, since the delivery path involving the femoral artery and vein is non-linear, and because an ultimate configuration of the delivery device is not coplanar, it is impossible for conventional delivery systems to allow both circumferential rotation and a constantly maintained configuration.

Solution to Problem

In view of the above problems with the conventional delivery systems, it is an object of the present invention to provide a novel prosthetic valve delivery catheter and device, which allow precise release of a prosthetic valve with an irregular cross-sectional shape.

According to one aspect of the present invention, there is provided a prosthetic valve delivery catheter, comprising an outer sheath assembly and an inner sheath assembly, the outer sheath assembly comprising a capsule in which a prosthetic valve can be received and an outer sheath fixedly connected at one end to the capsule, the inner sheath assembly comprising an inner sheath and an anchor fixedly connected to the inner sheath, the inner sheath assembly arranged within a lumen of the outer sheath assembly, the capsule and the anchor forming a circumferentially indexed fit therebetween.

Additionally, in the prosthetic valve delivery catheter, an inner wall of the capsule may be configured for engagement with an outer wall of the anchor.

Additionally, in the prosthetic valve delivery catheter, a protrusion or recess may be provided on or in the inner wall of the capsule, and a recess or protrusion that is complementary to the protrusion or recess in the inner wall of the capsule may be provided in or on the outer wall of the anchor.

Additionally, in the prosthetic valve delivery catheter, at least one embedded section may be provided in the outer wall of the anchor, and a friction generated between the embedded section and the capsule is greater than a friction generated between the prosthetic valve and the capsule.

Additionally, in the prosthetic valve delivery catheter, a coefficient of static friction between the embedded section and the capsule may range from 0.1 to 1.5.

Additionally, in the prosthetic valve delivery catheter, the embedded section may comprise a first strip unit and a second strip unit, with a first spring and a second spring being connected therebetween.

Additionally, the prosthetic valve delivery catheter may further comprise a pull thread, the pull thread is arranged at joints of the first and second strip units and the first or second spring, and drawn out of the inner sheath.

Additionally, in the prosthetic valve delivery catheter, the first and second strip units may be arranged in symmetry with respect to an axis of the outer wall of the anchor.

Additionally, in the prosthetic valve delivery catheter, the capsule may be connected to the outer sheath by a bearing or an elastic material.

Additionally, in the prosthetic valve delivery catheter, the outer sheath may be a polymer tube or a composite metal-polymer tube.

Additionally, in the prosthetic valve delivery catheter, the inner sheath may be a single-lumen tube or a multi-lumen tube.

According to another aspect of the present invention, there is provided a prosthetic valve delivery device, comprising a handle and the delivery catheter as defined above, which is coupled to the handle, the handle provided therein an outer sheath actuation member and an inner sheath actuation member, the outer sheath actuation member coupled to the outer sheath in order to actuate axial movement of the outer sheath, the inner sheath actuation member coupled to the inner sheath in order to actuate circumferential rotation of the inner sheath.

Additionally, the prosthetic valve delivery device may further comprise a pull thread, which is fixedly connected to the handle.

Compared with the prior art, in the prosthetic valve delivery catheter of the present invention, the circumferentially indexed fit between the capsule and the anchor allows them to rotate in concert with circumferential rotation of the inner sheath to adjust an alignment between the prosthetic valve and a native valve annulus so as to retain a three-dimensional configuration as required for positioning. Once the adjustment has completed, the capsule can be then driven by the outer sheath to move axially as required for release of the prosthetic valve.

In the figures, 1: a delivery catheter; 2: a handle; 3, a prosthetic valve; 11: a guide tip; 12: a capsule; 13: an outer sheath; 14: an anchor; 15: an inner sheath; 21: an outer sheath actuation member; 22: an inner sheath actuation member; 141: an embedded section; 1411: a first strip unit; 1412, a second strip unit; 1421, a first spring; 1422, a second spring; 142, a pull thread; and 143, a joint.

DETAILED DESCRIPTION

The above and other features, aspects and objects of the present invention will be more readily apparent from the following detailed description of specific embodiments thereof.

Figure 1:
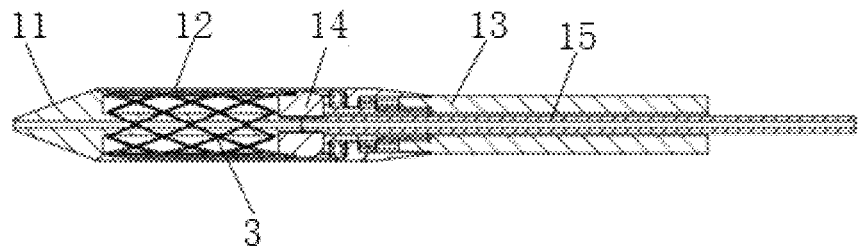
FIG. 1 is a structural schematic of a prosthetic valve delivery catheter according to an embodiment of the present invention.

As shown in FIG. 1, a prosthetic valve delivery catheter according to an embodiment of the present invention includes an outer sheath assembly and an inner sheath assembly. The outer sheath assembly includes a capsule 12 in which the prosthetic valve 3 can be received and an outer sheath 13 fixedly connected at one end to the capsule 12. The inner sheath assembly includes an inner sheath 15 and an anchor 14 fixedly connected to the inner sheath 15. The inner sheath assembly is arranged within a lumen of the outer sheath assembly.

Figure 2:
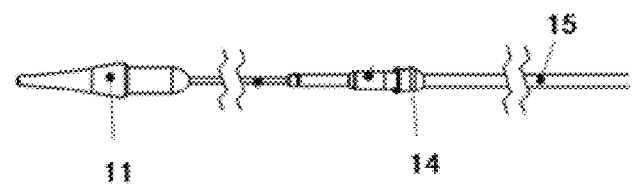
FIG. 2 is a structural schematic showing a guide tip and the composition of an inner sheath assembly according to an embodiment of the present invention.

As shown in FIGS. 1 to 2, the prosthetic valve delivery catheter according to the present invention may further include a guide tip 11 connected to the inner sheath 15. Preferably, the guide tip 11 has a streamlined outer contour, which can avoid the guide tip from scratching the inner wall of a blood vessel and can help in guiding the advancement of the entire delivery catheter through the blood vessel.

In implementations of the present invention, the fixed connection of the capsule 12 to the outer sheath 13 may be accomplished by a smooth transition so that an outer surface of the delivery catheter generally appears smooth. The capsule 12 may have an outer diameter that is equal to or greater than an outer diameter of the outer sheath 13. If there is a difference between the outer diameters of the capsule 12 and the outer sheath 13, the connection between the capsule 12 and the outer sheath 13 may be uniformly tapered proximally so that there is no bump, recess, step or the like in or on those two outer surfaces. The outer sheath 13 may be configured to drive axial movement of the capsule 12 as required for the loading or release of the prosthetic valve 3.

A circumferentially positioning fit is formed between the capsule 12 and the anchor 14. The inner sheath 15 may drive circumferential movement of the anchor 14, which may in turn cause the capsule 12 to move circumferentially as desired.

In specific implementations, since the inner sheath 15 is also coupled to the guide tip 11, the latter will also move with the inner sheath 15, while the outer sheath 13 still stays stationary, maintaining a three-dimensional configuration as required for positioning by the delivery catheter.

Figure 3:
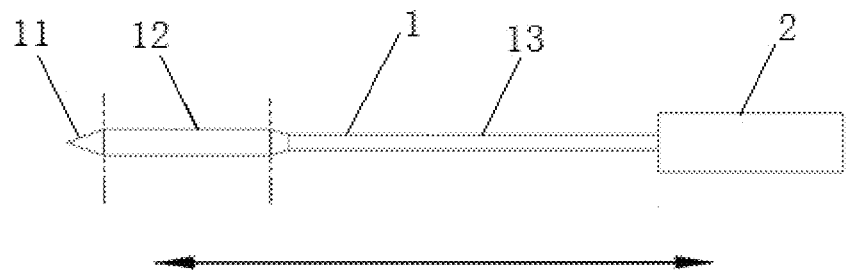
FIG. 3 is a structural schematic of a prosthetic valve delivery device according to an embodiment of the present invention.

As shown in FIG. 3, a prosthetic valve delivery device according to an embodiment of the present invention includes a handle 2 and a delivery catheter 1 coupled to the handle 2. In implementations of the present invention, movement toward the delivery catheter 1 is defined as distal movement and that toward the handle 2 as proximal movement.

Figure 4:
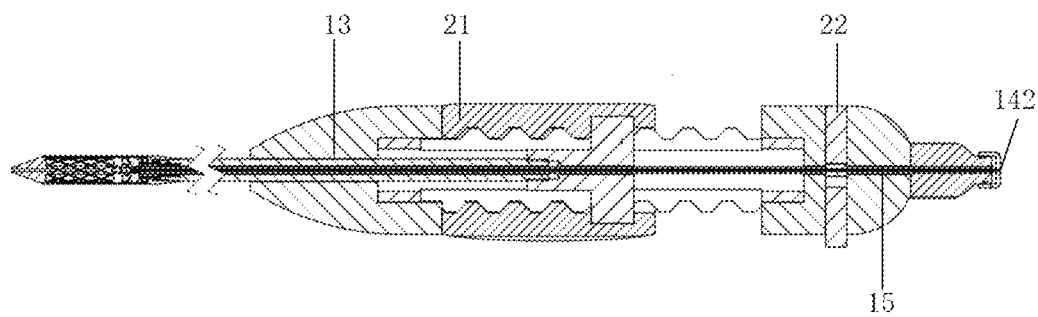
FIG. 4 is a structural schematic of a handle according to an embodiment of the present invention.

As shown in FIG. 4, the handle 2 may be provided therein with an outer sheath actuation member 21 and an inner sheath actuation member 22. The outer sheath actuation member 21 may be coupled to the outer sheath 13 in order to actuate axial movement of the outer sheath 13, and the inner sheath actuation member 22 may be coupled to the inner sheath 15 in order to actuate circumferential rotation of the inner sheath 15.

In specific implementations, the handle 2 may drive a bearing to move, thus resulting in circumferential rotation of the inner sheath actuation member 22. As a result, the inner sheath 15 may rotate, causing the anchor 14 and the capsule 12 to rotate in concert therewith and thereby adjusting and aligning the prosthetic valve 3 with a native valve annulus. After that, the handle 2 may drive the bearing to move to cause axial movement of the outer sheath actuation member 21. As a result, the outer sheath 13 drives the capsule 12 to move axially therewith relative to the inner sheath 15, allowing loading and release of the prosthetic valve 3.

Optionally, in embodiments of the present invention, the handle may be driven either electrically or manually.

Figure 5:
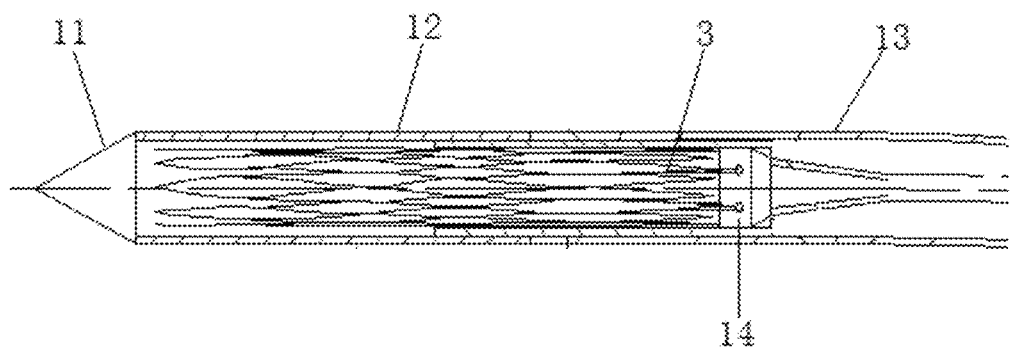
FIG. 5 is a cross-sectional view of a capsule in engagement with an anchor according to an embodiment of the present invention.
Figure 6:
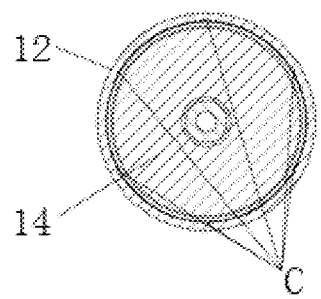
FIG. 6 is a structural schematic showing protrusions in engagement with respective complementary recesses, which are provided on and in the capsule and the anchor, according to an embodiment of the present invention.
Figure 7:
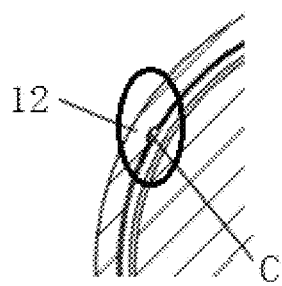
FIG. 7 is an enlarged view of a portion of FIG. 6 showing how the capsule is engaged with the anchor.

In embodiments of the present invention, the circumferentially positioning fit between the capsule 12 and the anchor 14 may be accomplished by either of the following methods:

1. Engagement of an inner wall of the capsule 12 with an outer wall of the anchor 14, as shown in FIG. 5, which allows circumferential immobilization of the capsule 12 with respect to the anchor 14. Specifically, as shown in FIGS. 6 to 7, a protrusion or recess (C) may be provided on or in the inner wall of the capsule 12, and a corresponding recess or protrusion that is complementary to the protrusion or recess on or in the inner wall of the capsule 12 may be provided in or on the outer wall of the anchor 14.

Optionally, the protrusion and recess on and in the inner wall of the capsule 12 and the outer wall of the anchor 14 may have a square, triangular, circular, irregular or other shape. Additionally, one or more such protrusions and, correspondingly, one or more such recesses may be provided.

Optionally, in case of multiple protrusions and recesses being provided, they may be either of the same or different shapes and distributed circumferentially on and in the outer wall of the anchor 14 and the inner wall of the capsule 12 uniformly or not. Preferably, multiple protrusions and recesses are uniformly distributed circumferentially on and in the outer wall of the anchor 14 and the inner wall of the capsule 12.

Although either of the capsule 12 and the anchor 14 may be provided with either of the protrusion(s) and recess(es) according to embodiments of the present invention, considering the capsule 12 has a relative small wall thickness, it is preferred that the protrusion(s) is/are provided on the inner wall of the capsule 12.

Figure 8:
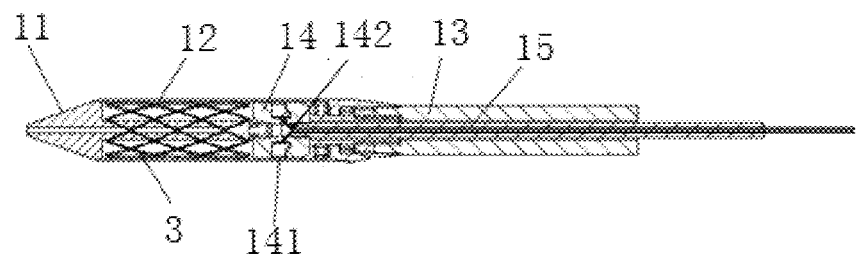
FIG. 8 is a cross-sectional view showing an embedded section in an outer wall of the anchor according to an embodiment of the present invention.

2. At least one embedded section 141 is arranged in the outer wall of the anchor 14, as shown in FIG. 8, which has a friction force with the capsule 12 that is greater than a friction force between the prosthetic valve 3 and the capsule 12 so that a friction force generated between the anchor 14 and the capsule 12 is greater than a force for releasing or re-capturing the valve. By virtue of the friction force, the capsule 12 and the anchor 14 can rotate in concert with each other.

Specifically, one or more sections of a high coefficient of friction material may be embedded in the outer wall of the anchor 14 and have an outer diameter that may vary as required for fiction-based locking to the capsule 12 and unlocking therefrom.

Preferably, in the prosthetic valve delivery device, a coefficient of static friction between the embedded section 141 and the capsule 12 ranges from 0.1 to 1.5.

Figure 9:
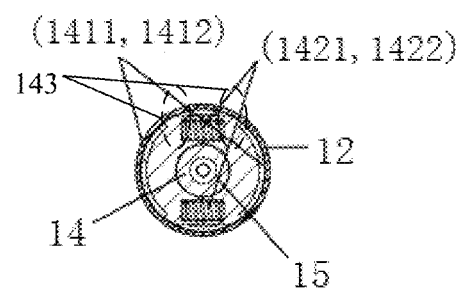
FIG. 9 is a structural schematic of an embedded section according to an embodiment of the present invention.

Further, as shown in FIG. 9, the embedded section 141 may include a first strip unit 1411 and a second strip unit 1412, with a first spring 1421 and a second spring 1422 connected therebetween.

Figure 10:
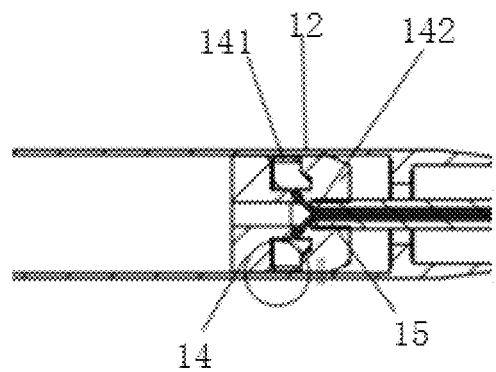
FIG. 10 is a schematic diagram showing the capsule and the anchor that are separated from each other as a result of tightening a pull thread according to an embodiment of the present invention.

Further, as shown in FIG. 10, a pull thread 142 may be further included, which is arranged at joints 143 of the first and second strip units 1411, 1412 and the first or second spring 1421. Additionally, the pull thread 142 may be drawn through the inner sheath 15 and tied to the handle 2.

Preferably, the pull thread 142 may consist of a single or multiple strands. Examples of the pull thread 142 may include, but are not limited to, a single solid metal wire or a thread consisting of multiple twisted metal strands. In implementations, the pull thread 142 may be axially pulled to change the outer diameter of the embedded section 141.

Figure 11:
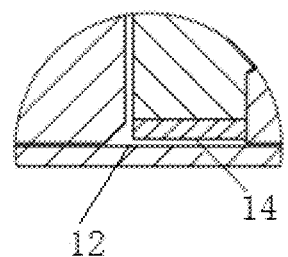
FIG. 11 is an enlarged view of a portion of FIG. 10 showing how the capsule and the anchor are separated from each other.
Figure 12:
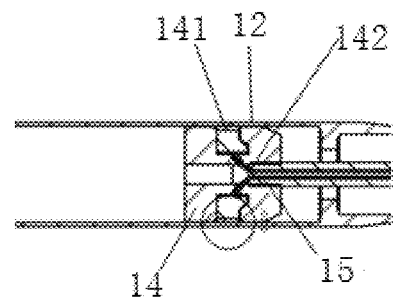
FIG. 12 is a schematic diagram showing the capsule and the anchor that are locked to each other as a result of loosening the pull thread according to an embodiment of the present invention.
Figure 13:
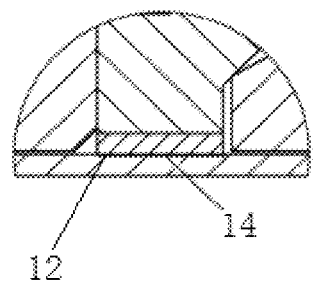
FIG. 13 is an enlarged view of a portion of FIG. 12 showing how the capsule and the anchor are locked to each other.

As shown in FIGS. 10 to 11, when the pull thread 142 is tightened, the first spring 1421 (or second spring 1422) may be compressed, bringing the first and second strip units 1411, 1412 of the embedded section 141 closer to each other. As a result, the anchor 14 may be separated from, and move independently of, the capsule 12. As shown in FIGS. 12 to 13, when the pull thread 142 is loosened, the first and second strip units 1411, 1412 of the embedded section 141 may move outward and abut against the capsule 12. As a result, the anchor 14 and the capsule 12 may be able to rotate in concert by virtue of a friction-based locking from the embedded section 141.

Preferably, in the prosthetic valve delivery device, the first and second strip units 1411, 1412 are arranged in symmetry with respect to an axis of the outer wall of the anchor 14. This facilitates connection of the pull thread 142 to all the embedded section(s) on a single side.

Optionally, the capsule 12 may be connected to the outer sheath 13 by a bearing or an elastic material. Examples of the elastic material may include, but are not limited to, silicone materials, PU materials, Pebax nylon elastomers (engineering polymers), etc. Preferably, the capsule 12 may be connected to the outer sheath 13 by a bearing, which allows free circumferential rotation therebetween. Alternatively, the capsule 12 may be connected to the outer sheath 13 by a spring or elastic material. In this case, circumferential rotation between the capsule 12 and the outer sheath 13 is only possible within an angular limit that depends upon the properties of the spring or elastic material.

According to embodiments of the present invention, the handle 2 may be manipulated to drive axial movement of the bearing and hence the outer sheath actuation member 21, which causes axial movement of the outer sheath 13 and hence the capsule 12 with respect to the inner sheath 15, thus allowing loading and release of the prosthetic valve 3. In addition, the handle 2 may be also manipulated to drive circumferential rotation of the bearing and hence the inner sheath actuation member 22, which causes the anchor 14 and the capsule 12 to rotate in concert with each other with the rotation of the inner sheath 15. In this way, the adjustment of the angle for releasing the prosthetic valve 3 can be achieved, thereby allowing precisely releasing the prosthetic valve 3.

Optionally, the outer sheath 13 may be a controllable bending tube, such as a polymer tube or a composite metal-polymer tube. In implementations, the outer sheath 13 may be a polymer tube with metal structure arranged in or on the inner surface thereof. The outer sheath 13 may be embedded therein with at least one metal wire, and controlling of bending angle, position and direction of the outer sheath 13 by pulling different metal wires. Preferably, multiple metal wires are embedded in the controllable bending tube in order to improve precision of the controlled bending.

Optionally, the inner sheath 15 may be a single-lumen tube or a multi-lumen tube. Preferably, the inner sheath 15 is a multi-lumen tube because in addition to the pull thread 142, a guide wire is also intended to be threaded through the inner sheath 15. In this case, the multi-lumen tube can provide separate channels for the pull thread 142 and the guide wire so that they can perform their own intended functions without affecting each other.

According to embodiments of the present invention, a process of loading the prosthetic valve may involve: retracting the capsule 12 by manipulating the handle 2 until a leading end of the capsule 12 is located behind the anchor 14 so that the anchor 14 is exposed; attaching the self-expanding prosthetic valve 3 to the anchor 14; and upon stabilization of the prosthetic valve 3, causing the outer sheath 13 to move forward until the prosthetic valve 3 is completely housed in the capsule 12, with its leading end abutting against the guide tip 11.

According to embodiments of the present invention, a process of delivering the prosthetic valve may involve: introducing the entire prosthetic valve delivery device over the guide wire into a patient's body via a puncture made therein; and delivering the capsule 12 with the prosthetic valve 3 crimped therein, through a path passing through the femoral vein and the atrial septum, to the diseased native valve annulus.

According to embodiments of the present invention, a process of releasing the prosthetic valve may involve: controlling the bending through the outer sheath 13, and when completing the adjustment, the outer sheath 13 is immobile; circumferentially rotating the inner sheath 15 by manipulating the handle 2 so that the anchor 14 and capsule 12 rotate in concert with each other with the rotation of the inner sheath 15, thereby adjusting the relative position between the prosthetic valve 3 and the native valve annulus so as to ensure good conformance of the prosthetic valve 3 to the native valve annulus; and upon the prosthetic valve 3 being circumferentially adjusted to the desired angular position, proximally moving the outer sheath 13 and hence the capsule 12 in the axial direction by manipulating the handle 2 until the prosthetic valve 3 is completely detached from the delivery device and released to a predetermined position.

Preferably, in embodiments of the present invention, the release of the prosthetic valve 3 may be suspended at any desired time to allow an additional positioning adjustment by circumferentially rotating the inner sheath 15. This facilitates real-time alignment and precise release of the prosthetic valve 3.

In summary, according to embodiments of the present invention, the capsule 12 may both axially move under actuation of the outer sheath 13 concurrently with the anchor 14 being kept stationary, and circumferentially rotate in concert with the anchor 14 under actuation of the inner sheath 15, concurrently with the outer sheath 13 being kept stationary. This is advantageous in allowing the capsule 12 to circumferentially move in concert with the anchor 14 and independently of the axial movement, and to move axially under actuation of the outer sheath 13 and independently of the circumferential movement.

According to embodiments of the present invention, with the delivery device being maintained in an overall configuration in which the outer sheath controls the bending in a desired manner, circumferential movement of the prosthetic valve is possible, thus allowing precise release of the prosthetic valve even if it has an irregular cross sectional shape.

While the fundamental principles, main features and advantages of the present invention has been presented and described above, it will be appreciated by those of ordinary skill in the pertinent art that the present invention is not limited to the embodiments disclosed hereinabove, which, together with the above description, serve to explain the principles of the present invention, and various changes and modifications can be made to the present invention without departing from the spirit or scope of thereof. Accordingly, all such changes and modifications are intended to also fall within the scope of the present invention as defined by the appended claims and equivalents thereof.

What is claimed is:

1. A prosthetic valve delivery catheter, comprising an outer sheath assembly and an inner sheath assembly, wherein: the outer sheath assembly comprises a capsule in which a prosthetic valve can be received and an outer sheath rotatably connected at one end to the capsule; the inner sheath assembly comprises an inner sheath and an anchor fixedly connected to the inner sheath; and the inner sheath assembly is arranged within a lumen of the outer sheath assembly, the capsule and the anchor forming a circumferentially indexed fit therebetween to allow them to rotate in concert with a circumferential rotation of the inner sheath, wherein an outer wall of the anchor is provided with at least one embedded section, and wherein a friction generated between the embedded section and the capsule is greater than a friction generated between the prosthetic valve and the capsule, and wherein the embedded section comprises a first strip and a second strip, and wherein each of a first spring and a second spring is connected between the first strip and the second strip.

2. The prosthetic valve delivery catheter according to claim 1, wherein a coefficient of a static friction between the embedded section and the capsule ranges from 0.1 to 1.5.

3. The prosthetic valve delivery catheter according to claim 1, further comprising pull thread(s), wherein the pull thread(s) is (are) arranged at joints where the first and second strips meet the first or second spring, and is drawn out of the inner sheath.

4. The prosthetic valve delivery catheter according to claim 3, wherein the first and second strips are arranged axisymmetrically on the outer wall of the anchor.

5. The prosthetic valve delivery catheter according to claim 1, wherein the capsule is connected to the outer sheath by a bearing or an elastic material.

6. The prosthetic valve delivery catheter according to claim 1, wherein the outer sheath is a polymer tube or a composite metal-polymer tube.

7. The prosthetic valve delivery catheter according to claim 1, wherein the inner sheath is a single-lumen tube or a multi-lumen tube.

8. A prosthetic valve delivery device, comprising a handle and the delivery catheter according to claim 1, wherein the delivery catheter is coupled to the handle, wherein the handle is provided therein an outer sheath actuation member and an inner sheath actuation member, wherein the outer sheath actuation member is coupled to the outer sheath in order to actuate an axial movement of the outer sheath, and wherein the inner sheath actuation member is coupled to the inner sheath in order to actuate a circumferential rotation of the inner sheath.

9. The prosthetic valve delivery device according to claim 8, further comprising a pull thread, wherein the pull thread is fixedly connected to the handle.

10. The prosthetic valve delivery device according to claim 8, wherein a coefficient of a static friction between the embedded section and the capsule ranges from 0.1 to 1.5.

11. The prosthetic valve delivery device according to claim 8, wherein the capsule is connected to the outer sheath by a bearing or an elastic material.

12. The prosthetic valve delivery device according to claim 8, wherein the inner sheath is a single-lumen tube or a multi-lumen tube.

* * * * *